US00PP08671P

United States Patent [19]

Austin

[11] Patent Number: Plant 8,671

[45] Date of Patent: Apr. 5, 1994

[54] ROSE PLANT AUSGLISTEN

[75] Inventor: David C. H. Austin, Albrighton, England

[73] Assignee: David Austin Roses Limited, Albrighton, England

[21] Appl. No.: 954,884

[22] Filed: Sep. 30, 1992

[51] Int. Cl.[5] ..... A01H 5/00

[52] U.S. Cl. ..... Plt./1

[58] Field of Search ..... Plt. 1, 26

*Primary Examiner*—Howard J. Locker
*Assistant Examiner*—E. F. McElwain
*Attorney, Agent, or Firm*—Klarquist, Sparkman, Campbell, Leigh and Whinston

[57] ABSTRACT

A shrub rose plant having small flowers and very bushy growth, and which repeat flowers very well.

1 Drawing Sheet

The present invention relates to a new and distinct variety of shrub rose plant of the *Rosa hydrida* class which was originated by me by crossing the variety Wife of Bath, with the variety Mary Rose.

The primary objective of this breeding was to produce a new rose variety having pink, quartered, scented flowers on a bushy plant which repeatedly flowers. The objective was substantially achieved along with other desirable improvements as evidenced by the following unique combination of characteristics which are outstanding in the new variety and which distinguish it from its parents, as well as from all other varieties of which I am aware:

1. Small flowers;
2. Repeat flowers very well; and
3. Very bushy growth.

Asexual reproduction of this new variety by budding, as performed at Albrighton, Wolverhampton, England, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Methuen Handbook of Colour, except where ordinary dictionary significance of color is indicated.

Parentage:

*Seed parent.*—Wife of Bath.

*Pollen parent.*—Mary Rose.

Classification:

*Botanical.*—*Rose hybrida.*

*Commercial.*—Shrub.

FLOWER

Observations made from specimens grown in a garden environment in Albrighton, Wolverhampton, England in August 1991.

Blooming habit: Recurrent.

Bud:

*Size.*—1¼" long when the petals start to unfurl.

*Form.*—The bud form is pointed ovoid, globular.

*Color.*—When sepals first divide, the bud color is greyish red 10C5 and brownish red 10C7. When half blown, the upper sides of the petals are mallow 12B5, and the base is buttercup yellow 4A7. The lower sides of the outer petals are pastel red 10A4, and the base is buttercup yellow 4A7.

*Sepals.*—Color: 29D7 with violet brown blush 10E6. Surface texture: Leathery. There are three normally appendaged sepals. There are two unappendaged sepals with hairy edges.

*Receptacle.*—Color: Greyish green 1D6, violet brown blush 10E7. Shape: Jug-shaped. Size: Small, about ¼"–⅜"×¼". Surface: Glandular.

*Peduncle.*—Length: Medium, averaging about 2–2½". Surface: Glandular. Color: Medium green. Strength: Erect.

Bloom:

*Size.*—Average open size is 2½" in diameter.

*Borne.*—Several together, in multiples of 3-clusters of irregular shape.

*Stems.*—Medium, normal. Average length is about 24 to 30".

*Form.*—When first open: Cupped. Permanence: Flattens, outer petals curl back.

*Petalage.*—Number of petals under normal conditions: 70 to 95.

*Color.*—The upper side of the petals is pale red 12A3, yellowing at base. The reverse side of the petals is pinkish white 11A2, yellowing at base. The base of the petals is pastel yellow 3A7. The major color on the upper side is pale red 12A3.

*Variegations.*—None.

*Discoloration.*—The general tonality at the end of the first day: Slightly greyer. At the end of the third day, reddish grey 12B2, yellowing to 3A2 at the base.

*Fragrance.*—Moderate.

Petals:

*Texture.*—Thin, soft and silky.

*Shape.*—Heart-shaped (trilobed apex), deltoid.

*Form.*—Tips slightly recurved, edges slightly quilled.

*Arrangement.*—Quartered. Inner petals curved inward and caught into the space between the perigynous zone and the style.

*Persistence.*—Petals hang on and dry.

*Lastingness.*—On the plant: Very long, 7 to 10 days. As a cut flower: Long, 5 to 7 days.

Reproductive parts:

*Anthers.*—Size: Medium. Quantity: Few (25–40). Color: Yellow. Arrangement: Tucked in calyx or partly so.

*Filaments.*—Color: Yellow.

*Pollen.*—Color: Gold yellow.

*Styles.*—Color: Yellowish white 1A2.

*Stigmas.*—Color: Yellowish white 1A2.

Form: Shrub.

Growth: Medium, branching, bushy.

Plant height: 36 to 42".

Foliage:

*Number of leaflets on normal mid-stem leaves.*—5.

*Size.*—Medium, about 2–2¾" long × 1¼–1½" wide.

*Quantity.*—Normal.

*Color.*—New foliage: Bracken green 29E7. Margin: Maroon 11F8. Old foliage: Dark green 29F7.

Leaflets:

*Shape.*—Base is round, pointed oval.

*Texture.*—Upper side: Leathery.

*Edge.*—Serrated.

*Serration.*—Double.

*Petiole rachis.*—Color: Green, violet brown blush 10E6.

*Petiole underside.*—With prickles, 2 to 3 per internode and glandular hairs.

*Stipules.*—Medium, about 1" long.

*Disease resistance.*—Resistant to mildew and blackspot under normal growing conditions at Albrighton, Wolverhampton, England.

Wood:

*New wood.*—Color: Light green, reddish greyish green 29D7, brownish red blush 10D7. Bark: Smooth.

*Old wood.*—Color: Greyish green 29D7. Bark: Smooth.

Prickles:

*Quantity.*—On main canes from base: Many. On laterals from main canes: Many.

*Form.*—Medium, hooked downward.

*Color when young.*—Brown.

*Position.*—Evenly distributed.

Small prickles:

*Quantity.*—On main stalks: Few. On laterals: Few.

*Color.*—Brown.

I claim:

1. A new and distinct shrub rose plant of the *Rosa hybrida* class, substantially as herein shown and described, characterized particularly as to novelty by the unique combination of its small flowers, repeat flowering very well, and very bushy growth.

* * * * *

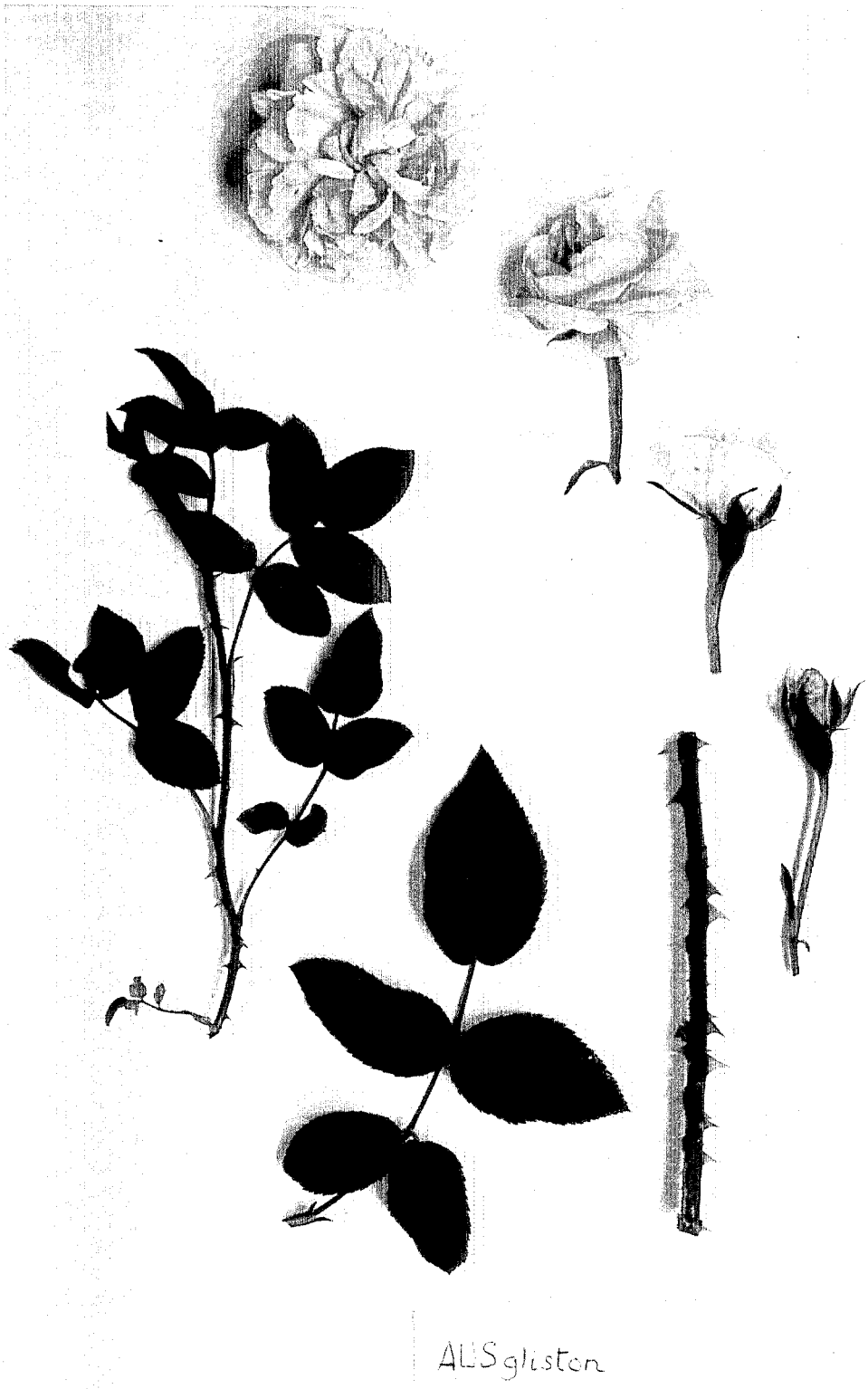
ALSgliston